United States Patent [19]

Klemann et al.

[11] Patent Number: 5,286,512
[45] Date of Patent: * Feb. 15, 1994

[54] DIOL LIPID ANALOGUES AS EDIBLE FAT REPLACEMENTS

[75] Inventors: Lawrence P. Klemann, Somerville; John W. Finley, Whippany; Anthony Scimone, Cedar Grove, all of N.J.

[73] Assignee: Nabisco, Inc., Parsippany, N.J.

[*] Notice: The portion of the term of this patent subsequent to May 16, 2006 has been disclaimed.

[21] Appl. No.: 690,743

[22] Filed: Apr. 24, 1991

Related U.S. Application Data

[63] Continuation-in-part of Ser. No. 372,689, Jun. 27, 1989, abandoned.

[51] Int. Cl.$^5$ .............................................. A23D 9/00
[52] U.S. Cl. ................................. 426/611; 426/804; 554/223; 554/227
[58] Field of Search ................. 426/601, 611, 531, 804

[56] References Cited

U.S. PATENT DOCUMENTS

| | | | |
|---|---|---|---|
| 519,980 | 5/1894 | Winter . | |
| 2,366,667 | 1/1945 | Deebel | 260/483 |
| 2,924,528 | 2/1960 | Barsky | 99/118 |
| 2,962,419 | 11/1960 | Minich | 167/81 |
| 2,976,245 | 3/1961 | Copes | 252/57 |
| 2,993,063 | 7/1961 | Godfrey | 260/410.6 |
| 3,495,010 | 2/1970 | Fossel | 424/312 |
| 3,579,548 | 5/1971 | Whyte | 260/410.7 |
| 3,600,186 | 8/1971 | Mattson et al. | 426/804 |
| 3,637,774 | 1/1972 | Babayan | 260/410.6 |
| 3,818,089 | 6/1974 | Bayley et al. | 424/9 |
| 3,876,794 | 4/1975 | Rennhard | 426/152 |
| 4,005,195 | 1/1977 | Jandacek | 424/180 |
| 4,304,768 | 12/1981 | Staub et al. | 424/180 |
| 4,508,746 | 4/1985 | Hamm | 426/601 |
| 4,582,927 | 4/1986 | Fulcher | 506/201 |
| 4,631,196 | 12/1986 | Zeller | 426/580 |
| 4,797,300 | 1/1989 | Jandacek et al. | 426/549 |
| 4,830,787 | 5/1989 | Klemann et al. | 260/410 |
| 4,840,815 | 6/1989 | Meyer et al. | 426/611 |
| 4,849,242 | 7/1989 | Kershner | 426/601 |
| 4,861,613 | 8/1989 | White et al. | 426/611 |
| 4,915,974 | 4/1990 | D'Amelia et al. | 426/611 |
| 4,925,692 | 5/1990 | Ryan | 426/531 |
| 4,927,659 | 5/1990 | Klemann et al. | 426/611 |

FOREIGN PATENT DOCUMENTS

| | | |
|---|---|---|
| 1106681 | 8/1981 | Canada ........................... 99/156 |
| 161114 | 5/1985 | European Pat. Off. . |
| 205273 | 5/1986 | European Pat. Off. . |
| 209770 | 1/1987 | European Pat. Off. . |
| 233856 | 2/1987 | European Pat. Off. . |
| 254547 | 7/1987 | European Pat. Off. . |
| 375031 | 12/1989 | European Pat. Off. . |
| 850610 | 9/1952 | Fed. Rep. of Germany . |
| 3529564 | 3/1987 | Fed. Rep. of Germany . |
| 1135647 | 3/1966 | United Kingdom . |
| 1293277 | 2/1970 | United Kingdom . |

OTHER PUBLICATIONS

Mattson et al. "Hydrolysis of fully esterified alcohols containing from one to eight hydroxyl groups by the lipolytic enzymes of rat pancreatic juice" 13 J. Lipid Res. pp. 325–328 (1972).
Bergelson et al., 116 Biochim. Biophys. Acta 511–520 (1966).
Booth and Gross, 40 JAOCS 551–553 (1963).
Brind et al., 84B Comp. Biochem. Physiol. 403–407 (1986).
Goodman & Gilman, 7th ed., Macmillan Pub. Co., N.Y. pp. 1002–1003 (1985).
Gurr and James, Lipid Biochemistry, 3rd ed., Chapman and Hall, New York, pp. 91–92 (1980).
Hamm, 49 J. Food Sci. 419–428 (1984).
Haumann, 63 JAOCS 278–288 (1986).
LaBarge, 42 Food Tech. 84–89 (1988).
Markley, Fatty Acids, 2d. ed., part 2, Krieger Pub. Co., pp. 785–797 (1983).
Smith et al., Principles of Biochemistry: General Aspects, 7th ed., McGraw-Hill, New York, p. 117 (1983).
Stryker, 31 Arch. Path. 670–692 (1941).
Nikkari and Haahti, 164 Biochem. Biophys. Acta. 294–305 (1968).
Okumura et al., 575 Biochem. Biophys. Acta. 156–165 (1979).
Radell and Brodman, 69 J. Phys. Chem. 928–932 (1965).

Primary Examiner—Carolyn Paden

[57] ABSTRACT

Diol lipid analogues, notably fatty acid diesters of various dihydric alcohols containing 4 to 10 carbon atoms, are physiologically compatible fat replacements for edible compositions. Preferred compounds are partially digestible.

22 Claims, No Drawings

DIOL LIPID ANALOGUES AS EDIBLE FAT REPLACEMENTS

This application is a continuation-in-part of U.S. Ser. No. 07/372,689, "Diol Lipid Analogues as Edible Fat Replacements" by Lawrence P. Klemann, John W. Finley and Anthony Scimone, filed Jun. 27, 1989, now abandoned.

BACKGROUND OF THE INVENTION

This invention relates to the use of diol lipid analogues, notably fatty acid esters of dihydric alcohols, as physiologically compatible fat replacements in foods and pharmaceuticals.

Although most lipids are derivatives of glycerol, many organisms of animal, plant and microbial origin also contain small amounts of lipids that are derivatives of diols. These include mono- and diacyl esters and mixed alkyl and alkenyl ester fatty acid derivatives of ethylene glycol, 1,2- and 1,3-propanediols, 1,3- 1,4- and 2,3-butanediols, and 1,5-pentanediol isolated from such widely differing tissues as mutton fat, fish liver, egg yolks, corn seeds, yeast and rat liver (Gurr, M. I., and James, A. T., *Lipid Biochemistry*, 3rd ed., Chapman and Hall, New York, 1980, pp. 91–92). These lipids, first separated from neutral lipid components using high-temperature gas-liquid chromatography, were named "diol lipids" (Bergelson, L. D., et al. 116 *Biochim. Biophys. Acta* 511 (1966)). Diol lipids have since been discovered among the ionic lipids (e.g., diol lipid analogues of phosphatidyl choline and phosphatidylethanolamine, diol choline plasma-logen, acylated diol galactosides, and diol lipoamino acids), and generally comprise a concentration of 0.5 to 1.5% that of glycerol derivatives (Smith, E. L., et al., *Principles of Biochemistry: General Aspects*, 7th ed., McGraw-Hill, New York, 1983, p. 117). Skin surface lipids can contain much higher concentrations (25–30% and above; see Nikkari, T., and Haahti, E., 164 *Biochim. Biophys. Acta.* 294 (1968) and Brind, J. L., et al. 84B *Comp. Biochem. Physiol.* 403 (1986)).

Diol lipids have not figured into reported research that has focused on ways of providing edible fat replacements, substances with the same functional and organoleptic properties as natural fat, but not the calories. (For recent reviews, see Hamm, D. J., 49 *J. Food Sci.* 419 (1984), Haumann, B. F., 63 *J. Amer. Oil Chem. Soc.* 278 (1986), and LaBarge, R. G., 42 *Food Tech.* 84 (1988).) A major strategy for developing low calorie replacement fats has been to structurally re-engineer the conventional triglycerides in such a way as to retain their conventional functional properties in foods, while removing their susceptibility toward hydrolysis or subsequent absorption during digestion. To this end, the ester linkages have been reversed (e.g., malonates in U.S. Pat. No. 4,482,927 to Fulcher and trialkoxytricarballylates in U.S. Pat. No. 4,508,746 to Hamm); the ester linkages have been replaced by ether linkages (U.S. Pat. No. 3,818,089 to Bayley and Carlson and Can. Pat. No. 1,106,681 to Trost; ethoxy and propoxy groups have been inserted between the fatty acids and the glycerol backbone (U.S. Pat. No. 4,861,613 to White and Pollard); the glycerol moiety has been replaced with alternate polyols (e.g., pentaerythritol in U.S. Pat. No. 2,962,419 to Minich, sugars in U.S. Pat. No. 3,600,186 to Mattson and Volpenhein and U.S. Pat. No. 4,840,815 to Meyer, et al., and polyglycerol in U.S. Pat. No. 3,637,774 to Babayan and Lehman); and the fatty acids have been replaced with alternate acids (e.g., branched acids as described in U.S. Pat. No. 3,579,548 to Whyte).

A second major approach to the development of a low calorie fat has been to explore or synthesize nonabsorbable polymeric materials structurally unlike triglycerides, but having physical properties similar to edible fat. Mineral oil was disclosed as early as 1894 (U.S. Pat. No. 519,980 to Winter), and, more recently, polydextrose (U.S. Pat. No. 4,631,196 to Zeller), polyglucose and polymaltose (U.S. Pat. No. 3,876,794 to Rennhard), polysiloxane (Eur. Pat. Ap. No. 205,273 to Frye), jojoba wax (W. Ger. Pat. No. 3,529,564 to Anika), polyoxyalkylene esters (U.S. Pat. No. 4,849,242 to Kershner), and polyvinyl alcohol esters (U.S. Pat. No. 4,915,974 to D'Amelia and Jacklin) have been suggested.

Nondigestible or nonabsorbable fat replacements have proved disappointing when tested in feeding trials, where gastrointestinal side effects occurred, in some cases so extreme that frank anal leakage was observed. Nondigestible fats appear to act as a laxative and are expelled from the body, eliciting foreign body reactions like those early documented for mineral oil (Stryker, W. A., Arch. Path. 31: 670–692 (1941), more recently summarized in Goodman and Gilman's *Pharmacological Basis of Therapeutics*, 7th ed., Macmillan Pub. Co., N.Y. 1985, pp. 1002–1003). In the U.S.D.A.'s assessment of the caloric availability and digestibility of a series of new-type fats in the 1960's (e.g., amylose fatty acid esters, diglyceride esters of succinic, fumaric, and adipic acids, and polymeric fats from stearic, oleic and short-chain dibasic acids; see Booth, A. N., and Gros, A. T., *J. Amer. Oil Chem. Soc.* 40: 551–553 (1963) and the references cited therein), rats fed the experimental fats exhibited undesirable gastrointestinal side effects similar to what had already been observed with mineral oil consumption by people. In several of the balance studies, the diarrhea was so extreme that digestibility coefficients could not be calculated (ibid., Table I, p. 552).

Polyglycerol and polyglycerol esters have been suggested, not only as fat replacements, but also as fecal softening agents (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, incorporating saturated fatty groups, Eur. Pat. Ap. No. 233,856 to Bernhardt, or mixing residues, U.S. Pat. No. 4,797,300 to Jandacek, et al.). Saturated fatty acids have been disclosed as antianal leakage agents for polyorganosiloxane fat substitutes (U.S. Pat. No. 4,925,692 to Ryan), and dietary fiber preparations have been incorporated into foodstuffs containing other fat replacements to help inhibit the diarrheal effect (U.S. Pat. No. 4,304,768 to Staub et al. and Eur. Pat. Ap. No. 375,031 to DeBoer and Kivits). Partially digestible fat replacements have also been suggested (U.S. Pat. No. 4,830,787 to Klemann and Finley; U.S. Pat. No. 4,849,242, cited above; and U.S. Pat. No. 4,927,659 to Klemann, et al.).

SUMMARY OF THE INVENTION

It is an object of this invention to suggest a new approach to the development of edible fat replacements. It is another object of this invention to suggest a new class of edible fat mimetics and food compositions incorporating them. It is another object of this invention to suggest edible fat mimetics that have minimal gastrointestinal side effects. It is a further object of this invention to provide reduced calorie lipids having excellent organoleptic properties and functional characteristics useful in a wide variety of foods.

These and other objects are accomplished by the present invention. Instead of altering triglyceride molecules or creating polymeric fatty substances foreign to natural lipids, the present invention describes edible fat replacements that are related to the minor lipid constituents of natural fat. The new class of fat replacements herein described are analogous to natural diol lipids, and, in a preferred embodiment, are partially digestible and, hence, more compatible with normal digestion than nondigestible fat replacements. The present invention also preferably provides fat replacement products having multiple fatty acid substituents, which, on ingestion, are incompletely hydrolyzed so that the product may be engineered to provide essential or desirable fatty acids.

The fat mimetic compounds of the present invention, referred to herein as diol lipid analogues, can be defined by the following structural formula:

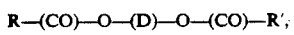
R—(CO)—O—(D)—O—(CO)—R', where D is an organic radical having 4 to 10 carbons, and R and R' are aliphatic groups having 1 to 29 carbons.

D is preferably an aliphatic group. The compounds of this invention are diols containing 4 to 10 carbon atoms esterified with two fatty acids.

DETAILED DESCRIPTION OF THE INVENTION

In the practice of this invention, diol lipid analogues, compounds which have at least two fatty acids esterified to a diol which is not ethylene glycol or glycerol, are partially digestible edible fat replacements. They mimic their natural counterparts, and, slowly hydrolyzed with at least one fatty acid cleaved off when they are digested, they are more physiologically compatible than nondigestible fat replacements.

This invention comprises compounds having the following general formula:

R—(CO)—O—(D)—O—(CO)—R', where D is an organic radical having 4 to 10 carbons. and R and R' are aliphatic groups having 1 to 29 carbons.

Organic radical D serves as a point of attachment for esterified aliphatic groups R and R'. Organic radical D is preferably an aliphatic group containing 4 to 10 carbon atoms, and may be linear or branched, saturated or unsaturated. Thus, this invention comprises compounds having a backbone of 4 to 10 carbon atoms to which are attached two aliphatic groups, R and R', in ester linkage to form physiologically compatible edible fat replacements.

The compounds of this invention comprise diols of the formula

HO—D—OH where D is as defined above, esterified with fatty acids of the formula RCOOH and R'COOH. Examples of diols forming the compound backbones (D) are normal and iso butanediols, butenediols, butynediols, normal, iso and neo pentanediols, pentenediols, pentynediols, normal, iso and neo hexanediols, hexenediols, heptanediols, heptenediols, octanediols, octenediols, octynediols, nonanediols, nonenediols, nonynediols, decanediols, decenediols, decynediols, and the like. The diols may be linear or branched, and may have hydroxyl substituents vicinal or distal, i.e., alpha, beta, gamma, delta, epsilon, or farther removed from one another. D is saturated, i.e., an alkyl group, in some embodiments. Chemical descriptions and formulae used herein include isomeric variations.

Esterified to the diols are fatty acids, RCOOH and R'COOH, which supply the R and R' aliphatic groups in the formulae above. The term "fatty acids" used here means organic fatty acids of the formula RCOOH and R'COOH having 1 to 30 carbons but containing a sufficient number of carbon atoms to provide for the physical properties commonly attributed to edible fats and oils. Fatty acids may be synthetic or natural, saturated or unsaturated, with straight or branched chains, and have from 2 to 30 carbon atoms. Examples of fatty acids are acetic, propionic, butyric, caproic, caprylic, pelargonic, capric, undecanoic, lauric, myristic, palmitic, stearic, arachidic, behenic, lignoceric, cerotic, montanic, palmitoleic, oleic, elaidic, vaccenic, linoleic, linolenic, eleostearic, arachidonic, erucic, brassidic, nervonic, eicosapentaenoic, docosatetraenoic, docosapentaenoic, docosahexaenoic, and the like acids.

Mixtures of fatty acids may also be used, such as those obtained from non-hydrogenated, partially hydrogenated or hydrogenated sunflower, high oleic sunflower, safflower, soybean, olive, sesame, peanut, palm kernel, cottonseed, mustard seed, palm, babassu nut, canola, rice bran, corn, rapeseed, high erucic rapeseed, low erucic rapeseed, borage, shea, meadowfoam, marine or other natural or processed oils. Non-hydrogenated, partially hydrogenated or hydrogenated fats such as dairy butter, tallow and lard, or plant waxes such as jojoba may be used to derive R and R' groups. Specific fractions of natural or processed oils, fats, or waxes may also be used.

At least one R or R' generally has 3 to 29 carbon atoms (from fatty acids having 8 to 30 carbons as described above), and the remainder will be selected to provide a discernible fatty character in the compounds. Thus, most of the R and R' groups have 3 or more carbon atoms (from fatty acids having 4 or more carbons). Typically, a majority of the R and R' groups will have 3 to 22 carbons (derived from acids having 4 to 23 carbons), more narrowly, 9 to 19 carbons (from acids having 10 to 20 carbons), and even more narrowly 15 to 17 carbons (from acids having 16 to 18 carbons). The R and R' groups can be aliphatic groups derived from natural oils, for example, safflower, sunflower, corn or soybean oil, and can comprise 98% or more of the R and R' groups have 15 to 17 carbons, with 80% or more having 17 carbons (derived from 18-carbon fatty acids).

The preferred diol lipid analogues of this invention are partially digestible, typically providing from about 0.5 to 8.5 kcal/gram, more narrowly 1.0 to 6.0 kcal/gram, even more narrowly 1.0 to 3.0 kcal/gram. In these preferred compounds, the fatty acid residues show differential reactivity toward enzymatic or chemical hydrolysis, so that the compounds become more hydrophilic when catabolized. The cleaved residue R or R' can be an essential or nutritionally desirable fatty acid such as linoleic acid or linolenic acid. The cleaved residue R or R' can also be derived from a fatty acid other desirable properties, such as, for example, a conjugated linoleic acid isomer.

The compounds of this invention may be prepared using standard esterification techniques for di- and polyhydric alcohols (reviewed in Markley, K. S., *Fatty Acids.* 2d. ed., part 2, Krieger Pub. Co., 1983, pp. 785-797). These include reactions of the fatty acids, or fatty acid derivatives, for example, fatty acid chlorides or fatty acid anhydrides, with diols, or transesterification between fatty acid esters (e.g., fatty acid methyl esters) and the alcohols for such time under such conditions that the diol lipid analogues form. Starting materials may be obtained commercially or isolated from natural sources. Example preparations are set out in the next section.

A solvent may be employed in the syntheses. The term "solvent" means any material, including the reactants, that is liquid at the synthesis reaction temperature and pressure and will dissolve, suspend or hold the reactants in the reaction mixture in an amount effective to expedite contact for the desired esterification reaction to occur. Sample syntheses for some diol lipid analogues of this invention are included in the Examples section.

Some diols esterified with fatty acids have been used in the past as surfactants or lubricants. Specific synthetic procedures following the general esterification outlined in Markley, supra, for these individual compounds have been published. For example, 2-butene-1,4-diol dilaurate was made in Example 5 of U.S. Pat. No. 2,366,667 to Deebel; dimerized linoleic acid esters of 1,4-butanediol were suggested after Example 2 of U.S. Pat. No. 2,976,245 to Copes; and 2-butene-1,4-diol dilinoleate was made in Example 2 of W. Ger. Pat. No. 850,610 to Krzikalla. Similarly, long chain butynediol esters were synthesized by Radell, J., and Brodman, B. W., 69 *J. Phys. Chem.* 928 (1965) and in EP 209,770 to Maignan, Lang, Restle, and Colin. Oleyl diesters of a number of aliphatic diols have also been synthesized using four microbial lipases (Okumura, S., et al. 575 *Biochim. Biophys. Acta.* 156 (1979)).

It is an advantage of this invention that the physical properties of diol lipid analogue fat mimetics can be varied over wide ranges by judicious selection of the backbone (D) and the fatty constituents (R and R'). Formulations for chocolate or confectionery applications, for example, can employ groups or components yielding high (e.g., above $\sim 30°$ C.), sharply melting mixtures, salad oils can employ groups or components yielding low to medium melting (e.g., melting $\sim 5°$ to $20°$ C.) mixtures that do not readily crystallize upon refrigeration, margarines and shortenings can employ groups or components yielding plastic mixtures, bakery products may employ groups or components stable to oxidation on storage, and so forth.

Broadly speaking, the diol lipid analogues of this invention can be employed as hardstocks or plastic fats in fat-containing edible emulsions comprising an oil phase and an aqueous phase, including those high in fat, such as margarines and cheeses, and those high in water, such as low fat spreads. Diol lipid analogues can be employed in dairy, meat, nut, egg, and other food products having a high natural fat component, and in vegetable, cereal and other products having a low natural fat component. Diol lipid analogues can be employed as ingredients for all types of leavened baked products, both yeast raised and chemically leavened, and unleavened baked products, and as coatings or coating ingredients for the same types of products, as well as for snack food products. In addition, diol lipid analgoues can be employed to form edible barrier layers, either on the exposed surfaces of foods or as internal barrier layers used to separate various portions of a food product, e.g., as a barrier between a dessert filling and an outer edible shell.

The diol lipid analogues of this invention may be incorporated either alone, or in combination with another fat (for example, admixed with a natural oil such as soybean, corn, safflower or sunflower oil, or a mixture of oils) and/or another fat mimetic, into any food composition or used in conjunction with any edible material. Other fats include natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like, or fractions thereof. Other fat mimetics include any heretofore suggested as edible fat replacements, including, but not limited to, sugar esters, neoalkyl esters, polyglycerol esters, malonate esters, ethoxylated and propoxylated glycerols, retrofats, carboxy/ carboxylates, polyvinyl alcohol esters and the like.

The term "edible material" is broad and includes anything edible. Representative of edible materials which can contain the diol lipid analogues of this invention in full or partial replacement of the normal fat component are: frozen desserts, e.g., frozen novelties, ice cream, ices, sherbet, or milk shakes; puddings and pie fillings; margarine and margarine substitutes and blends; flavored bread or biscuit spreads; mayonnaise; mustard; salad dressings; filled dairy products such as filled cream or filled milk; dairy or non-dairy cheese spreads; coffee lighteners, liquid and dried; flavored dips; frying fats and oils; reformed and comminuted meats; meat substitutes or extenders; nut products such as peanut butter; whipped toppings; compound coatings; frostings and fillings; cocoa butter replacements or blends; candy, especially fatty candies such as those containing peanut butter or chocolate; chewing gum; bakery products, e.g., cakes, breads, rolls, pastries, cookies, biscuits, and savory crackers; mixes or ingredient premixes for any of these; as well as flavor, nutrient, drug or functional additive delivery systems.

In one of its broad aspects, the invention provides a process for preparing a food product with reduced calories comprising adding a diol lipid analogue of the invention to at least one other food ingredient in the preparation of the food. The diol lipid analogue can be in total or partial substitution of the normal or natural fat content. Typical food ingredients will be selected from the group consisting of protein, carbohydrates, fats, nutrients and flavors. These ingredients are typically added in the form of flours, meals, fruits, dried fruits, vegetables, dried vegetables, meats, dried meats, starches, spices, salt, dried milk solids, sugars, acidulents, buffers, emulsifiers, stabilizers, gums, hydrophilic colloids, salts, antioxidants, colors, preservatives and the like. The fat mimetic will typically be employed in an amount of at least 5%, typically from 10 to 90% of the composition, and one or more other food ingredients will be present at 10 to 90%. More specific ranges, appropriate for various products, are given in the Examples.

In the practice of this invention, diol lipid analogues are desirably added to edible compositions in amounts effective to provide a significant caloric reduction of the calories due to fat. Typically, at least 5% of the normal fat component of a fat-containing edible composition is replaced by diol lipid analogues of this invention. A 10% or greater replacement is more effective for this purpose, and replacements of at least 25%, more particularly 50 to 100%, are desired in many cases.

Diol lipid analogues may be mixed with other fats or fat mimetics. An advantage of the present invention is that diol lipid analogues may be mixed with unsaturated natural oils so that desirable ratios of unsaturated to saturated residues in the food compositions are achieved. In one embodiment, the diol lipid analogues of this invention are mixed with natural oils such that the ratio of unsaturated to saturated residues in the resulting blend lies between 1 and 10, more narrowly between 2 and 6, and even more narrowly between 3 and 5. In one embodiment, the polyunsaturated to saturated ratio is above 2.5; in another, between 2.5 and 10; in another, between 10 and 25. The ratio can be increased by blending a less digestible fat mimetic with a highly polyunsaturated oil such as safflower, sunflower, sorghum, soybean, peanut, corn, cottonseed and sesame oils.

It is a further advantage of the invention that desirable physical properties can be achieved in foods containing high concentrations of naturally-occurring cis monounsaturates by blendinq the fat mimetics with oils rich in these, such as corn, soybean, canola, peanut, and cottonseed oils, and tallow, lard, and mixtures and fractions of these. Alternatively, it is possible to employ fatty acids or mixtures of fatty acids from fractions of one or more of these oils to supply the R and R' groups in the fat mimetics.

The following is a list of representative, but non-limiting, examples of diol lipid analogues of this invention:

(1) 1,4-But-2-enyl Dioleate

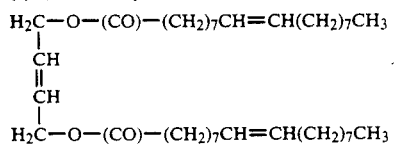

(2) 1,4-But-2-enyl Dimyristate

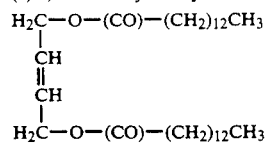

(3) 1,4-But-2-enyl Di-10-undecenate

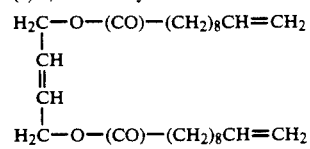

(4) 1,4-But-2-ynyl Dioleate

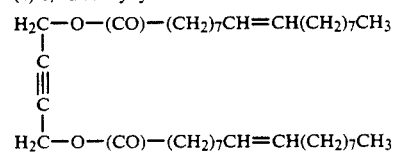

(5) 1,4-But-2-ynyl Dimyristate

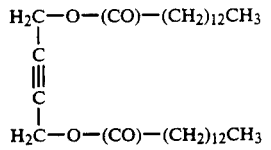

(6) 1,4-But-2-ynyl Distearate

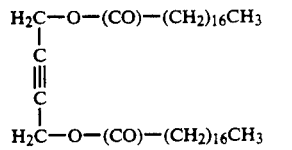

(7) 1,2-Pentyl Di-10-undecenate

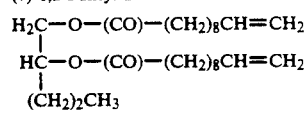

(8) 1,2-Pent-3-enyl Dioleate

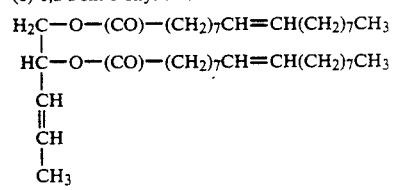

(9) 1,2-Pent-3-enyl Dipalmitate

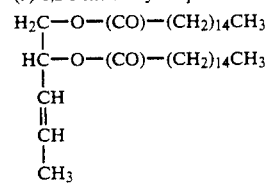

(10) 2-Methyl-1,3-propyl Dioleate

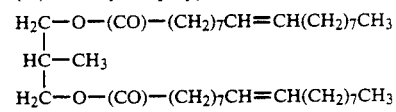

(11) 2-Methyl-1,3-propyl Di-10-undecenate

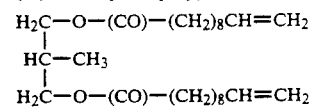

(12) 2-Methyl-1,3-propyl Dimyristate

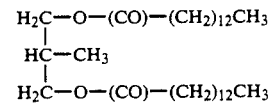

(13) 2-Ethyl-1,3-propyl Dioleate

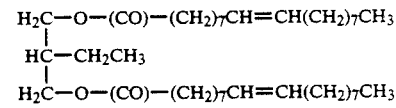

(14) 2-Diethyl-1,3-propyl Dioleate

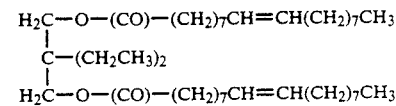

(15) 2-Diethyl-1,3-propyl Di-10-undecenate

-continued

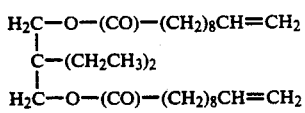

(16) 2-Methyl-2-propyl-1,3-propyl Palmitate-Oleate

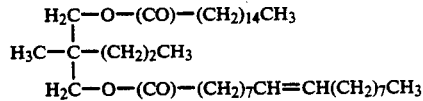

(17) 1,2-Butyl Dioleate

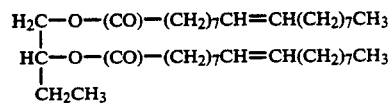

(18) 1,2-Pentyl Dioleate

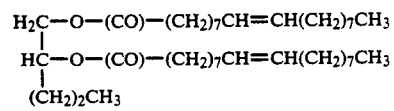

(19) 1,2-Hexyl Dioleate

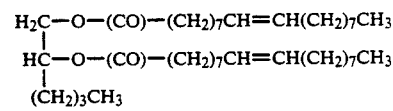

(20) 1,2-Octyl Dioleate

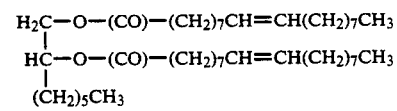

(21) 1,2-Decyl Dioleate

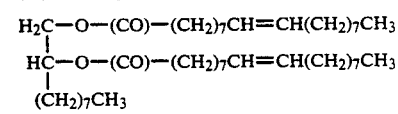

(22) 2-Methyl-2-propyl-1,3-propyl Oleate-10-Undecenate

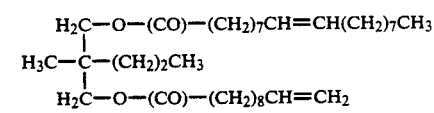

(23) 1,2-Hex-3-enyl Dioleate

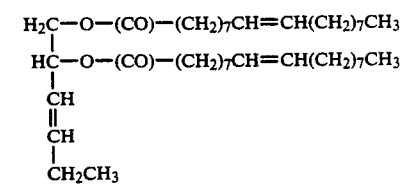

(24) 1,2-Decyl Dimyristate

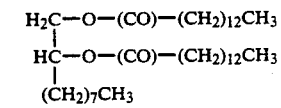

(25) Soybean 1,3-Non-5-enyl Diester

-continued

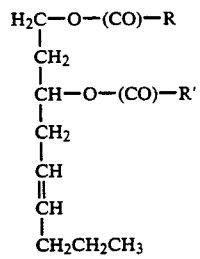

where R and R' are derived from soybean oil

EXAMPLES

The following examples are presented to further illustrate and explain the present invention and should not be taken as limiting in any regard. Unless otherwise indicated, all parts and percentages are by weight, and are based on the weight at the particular stage of the processing being described. The proton NMR spectra have assigned chemical shifts, multiplicities, and intensities consistent with the structures for which they are reported.

EXAMPLE 1

2-Methyl-2-propyl-1,3-propyl di-10-undecenate (also called 2,2-bis(10-undecenoyloxymethyl)pentane), a diol lipid analogue of this invention, is prepared in this example.

To a solution of 1.32 g. (0.01 mole) 2-methyl-2-propyl-1,3-propanediol in 30 mL pyridine is added 5 mL of 10-undecenoyl chloride. The reaction mixture is shaken for 4 hours at ambient temperature, filtered through silica, concentrated and refiltered to afford an oil.

Proton NMR Spectra in $CDCl_3$: chemical shift in ppm (multiplicity, intensity, assignment): 5.79 (multiplet, 2 H, HC=), 4.95 (multliplet, 4 H, =$CH_2$), 3.89 (singlet, 4 H, $CH_2$—O), 2.29 (triplet, 4 H, $O_2$C—C—$CH_2$), 1.30 (multiplet, 24 H, $CH_2$), and 0.90 (overlapping singlet and multiplet, 6 H, $CH_3$).

EXAMPLE 2

Another diol lipid analogue of this invention, 2-diethyl-1,3-propyl di-10-undecenate (also called 3,3-bis (10-undecenoyloxymethyl)pentane) is prepared in this example.

To a solution of 2,2-diethyl-1,3-propanediol (1.32 g., 0.01 mole) in 30 mL pyridine is added 5 mL of 10-undecenoyl chloride. The reaction mixture is shaken for 4 hours at ambient temperature, filtered through silica, and concentrated to give an oil.

Proton NMR Spectra in $CDCl_3$: chemical shift in ppm (multiplicity, intensity, assignment): 5.79 (multiplet, 2 H, HC=), 4.95 (multliplet, 4 H, =$CH_2$), 3.91 (singlet, 4 H, $CH_2$—O), 2.29 (triplet, 4 H, $O_2$C—C—$CH_2$), 2.02 (quartet, 4 H, $CH_2$—C=C), 1.60 (multiplet, 4 H, $O_2$C—$CH_2$), 1.35 (multiplet, 24 H, $CH_2$), and 0.83 (multiplet, 6 H, $CH_3$).

EXAMPLE 3

1,4-But-2-enyl dioleate (also called 1,4-bis(cis-9-octadecenoyloxy)but-2-ene), another diol lipid of this invention, is synthesized in this example.

To a solution of 8.8 g. (0.01 mole) cis-2-buten-1,4-diol in 20 mL pyridine is added 6.66 mL (0.02 mole) oleoyl chloride. The reaction mixture is shaken overnight at ambient temperature, filtered, concentrated, and refiltered to afford a yellow oil.

EXAMPLE 4

1,4-But-2-ynyl dioleate (also called 1,4-bis(cis-9-octadecenoyloxy)but-2-yne), another diol lipid of this invention, is synthesized in this example.

To a solution of 1,4-butynediol (8.6 g., 0.01 mole) in 20 mL pyridine is added 6.66 mL (0.02 mole) oleoyl chloride. The reaction mixture is shaken at ambient temperature overnight, filtered, concentrated and refiltered to afford an oil.

EXAMPLE 5

1,4-But-2-enyl dimyristate (also called 1,4-bis-myristoyloxy)but-2-ene), another diol lipid analogue of this invention, is synthesized in this example.

To a solution of 8.8 g. (0.01 mole) cis-2-buten-1,4-diol in 20 mL pyridine is added 4.9 g. (0.02 mole) myristoyl chloride. The reaction mixture is shaken overnight at ambient temperature, filtered, concentrated, and, once melted, refiltered. Upon cooling to room temperature, a solid is obtained.

EXAMPLE 6

1,2-Decyl dimyristate, another diol lipid analogue of this invention, is synthesized in this example.

1,2-Decanediol (3.5 g, 0.02 mole) and myristoyl chloride (10 g, 0.041 mole) in a flask containing a magnetic stir bar and fitted with a thermometer and a vacuum adapter. The solution is mixed under vacuum and warmed to 100° C. for 4 hours. Upon cooling to room temperature, a solid is obtained.

EXAMPLE 7

1,2-Butyl dioleate also called (1,2-bis(cis-9-octadecenoyloxy)butane), another diol lipid analogue of this invention, is prepared in this example.

To a solution of 0.90 g (0.01 mole) of 1,2-butanediol in 20 mL pyridine is added 6.02 g (0.02 mole) of oleoyl chloride. The reaction mixture is shaken overnight at ambient temperature, filtered, concentrated and refiltered through silica to afford the title compound.

EXAMPLE 8

1,2-Pentyl dioleate (also called 1,2-bis(cis-9-octadecenoyloxy)pentane), another diol lipid analogue of this invention, is prepared in this example.

To a solution of 1.04 g (0.01 mole) of 1,2-pentanediol in 20 mL pyridine is added 6.02 g (0.02 mole) of oleoyl chloride. The reaction mixture is shaken overnight at ambient temperature, filtered, concentrated and refiltered through silica to afford the title compound.

EXAMPLE 9

1,2-Hexyl dioleate (also called 1,2-bis(cis-9-octadecenoyloxy)hexane), another diol lipid analogue of this invention, is prepared in this example.

To a solution of 1,2-hexanediol in 20 mL pyridine is added 6.02 g (0.02 mole) of oleoyl chloride. The reaction mixture is shaken overnight at ambient temperature, filtered, concentrated and refiltered through silica to afford the title compound.

EXAMPLE 10

1,2-Octyl dioleate (also called 1,2-bis(cis-9-octadecenoyloxy)octane), another diol lipid analogue of this invention, is prepared in this example.

To a solution of 1.46 g (0.01 mole) of 1,2-octanediol in 20 mL pyridine is added 6.02 g (0.02 mole) of oleoyl chloride. The reaction mixture is shaken overnight at ambient temperature, filtered, concentrated and refiltered through silica to afford the title compound.

EXAMPLE 11

1,2-Decyl dioleate (also called 1,2-bis(cis-9-octadecenoyloxy)decane), another diol diester of this invention, is prepared in this example.

To a solution of 1.74 g (0.01 mole) of 1,2-decanediol in 20 mL pyridine is added 6.02 g (0.02 mole) of oleoyl chloride. The reaction mixture is shaken overnight at ambient temperature, filtered, concentrated and refiltered through silica to afford the title compound.

EXAMPLE 12

This example outlines the procedure for estimating the in vitro digestibility of the diol lipid analogues of this invention using pancreatic lipase.

Preparation of Reagents and Materials

1. Buffer: A pH 7.1 phosphate buffer is prepared by dissolving 6.8 g. $KH_2PO_4$ in 1 L. of millipore filtered water (to yield 0.05M phosphate). Fifty mg. $Ca(NO_3)_2$ and 5.0 g. cholic acid (Na salt, an ox bile isolate from Sigma) are added to give 300 microM $Ca^{++}$ and 0.5% cholic acid in 0.05M phosphate. The pH is adjusted to approximately 7.1 with solid NaOH. Several drops of Baker "Resi-analyzed" toluene are added to prevent bacterial growth during storage at 3°–5° C.

2. Lipase: About 15 mg./mL commercial porcine pancreatic lipase from U.S. Biochemical Corporation is dissolved in buffer.

3. Substrates and Standards: A 1.0 mL volumetric flask is charged with an amount of lipid substrate (test substance or standard) calculated to give a concentration of 200 nanomoles per microliter in Baker "Resi-analyzed" toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on TLC plates (prewashed with 1:1 chloroform/methanol) by diluting the substrate solution with 10:1 toluene (1 part substrate plus 9 parts toluene) in septum vials.

Procedure

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control, this amounts to 20 nanomoles of substrate spotted on the plate.) Develop with a suitable solvent system, for example, hexane:ethyl ether:acetic acid in a ratio of 60:40:1. After 15 cm elution, dry plate with a heat gun and determine amounts of starting substrate and products of hydrolysis by scanning 10 to 20 nanomoles per channel at a wavelength of 190 nm using the CAMAG TLC Scanner II densitometer equipped with a Spectra Physics 4270 integrator and comparing with controls run at the same time.

Results

Using this procedure and enzyme system, triolein is substantially hydrolyzed in 10 minutes. Under the same conditions, 1,4-but-2-enyl dioleate synthesized in Example 3 is about 20% hydrolyzed in three hours.

EXAMPLE 13

Sweet Chocolate. A low calorie sweet chocolate may be prepared by combining:

| Ingredient | parts |
| --- | --- |
| Cocoa Powder | 1.0 |
| Sugar | 1.0 |
| To this is added a portion of | |
| Diol Diester of Example 5 | 1.0 | and the ingredients are mixed thoroughly and passed through a refiner to reduce the particles to desired size. The material is conched, and the remaining diol diester is added. The mixture is poured into molds and quench cooled. No tempering regimen is necessary.

Chocolate Chips. The chocolate prepared above may be melted and deposited into nibs in the usual process.

EXAMPLE 14

Sugar Cookies. Sugar cookies may be prepared by blending:

| Ingredient | parts |
| --- | --- |
| Sugar | 231 |
| Example 7 Diol Diester | 114 |
| Salt | 3.7 |
| Sodium Bicarbonate | 4.4 |
| Water | 37.4 |
| 5.9% Dextrose Solution (wt/wt) | 58.7 |
| Flour | 391 |

All of the ingredients are creamed together. The dough so formed may be extruded (the dough is very tacky) and baked by the usual process.

EXAMPLE 15

Margarine. Margarine may be prepared by combining the ingredients for the following two phases:

| | parts |
| --- | --- |
| Oil Phase Ingredients | |
| Example 3 Diol Diester | 59.0 |
| Soybean Hardstock (IV 65) | 40.0 |
| Emulsifier | 1.0 |
| Aqueous Phase Ingredients | |
| Water | 95.8 |
| Milk Solids | 2.0 |
| Salt | 2.0 |
| Citric Acid | 0.1 |
| Beta Carotene | 0.1 |

The phases are emulsified in an oil:aqueous phase ratio of 80:20, and passed through a cool scraped surface heat exchanger in the usual process.

EXAMPLE 16

Flovor Bits. Flavor bits for incorporating into baked goods may be prepared by combining the following ingredients:

| Ingredient | parts |
| --- | --- |
| Sucrose | 215 |
| Water | 180 |
| Corn Syrup | 160 |
| Example 15 Margarine | 28 |
| Flavor | 12 |
| Citric Acid | 10 |
| Glycerine | 8 |
| Salt | 5 |
| Dye | 1 |

The first three ingredients are heated to 290° F. and the heat removed. Margarine is mixed in, and the mixture allowed to cool to 160°–170° F. before adding the remaining ingredients. (Almost any flavoring material may be used as flavor, for example, butterscotch or nut.) The mixture is then poured into a cold aluminum pan and frozen in dry ice. The frozen mixture is then cracked and milled into bits.

EXAMPLE 17

Butterscotch Cookies. Butterscotch cookies may be prepared by blending:

| Ingredient | parts |
| --- | --- |
| Flour | 22.0 |
| Example 4 Diol Diester | 20.0 |
| Salt | 0.7 |
| Sodium Bicarbonate | 0.1 |
| Monocalcium Phosphate | 0.1 |
| Vanillin | 0.1 |
| Water | 8.0 | and mixing well. To this is added

| | |
| --- | --- |
| Sugar | 30.0 | which is mixed until dispersed. Then

| | |
| --- | --- |
| Example 16 Butterscotch Bits | 19.0 | are added and mixed until just blended prior to depositing and baking in the usual process.

EXAMPLE 18

Vanilla Wafers. To prepare vanilla wafers, blend:

| Ingredient | parts |
|---|---|
| Example 8 Diol Diester | 25 |
| Flour | 100 |
| Granulated Sugar | 72 |
| High Fructose Corn Syrup | 5.0 |
| Nonfat Dry Milk | 1.0 |
| Salt | 1.0 |
| Ammonium Bicarbonate | 0.1 |
| Dried Egg Yolk | 1.0 |
| Water | 55 |

The dough so formed may be rolled, wire cut to ¼ inch thickness, and baked by the usual process to give a vanilla wafer cookie.

EXAMPLE 19

Chocolate Chip Cookies. Chocolate chip cookies may be prepared using the butterscotch cookie recipe of Example 18, but substituting

| Ingredient | parts |
|---|---|
| Example 15 Margarine | 10.0 |
| Example 9 Diol Diester | 10.0 | for the fat mimetic ingredient

| | |
|---|---|
| Granulated Sugar | 15.0 |
| Brown Sugar | 15.0 | for the sugar, and

| | |
|---|---|
| Example 13 Chocolate Chips | 19.0 | for the butterscotch bits.

EXAMPLE 20

Filled Cream. To make a "filled cream" composition, homogenize about

| Ingredient | parts |
|---|---|
| Example 1 Diol Diester | 30 |
| Skim Milk | 82 |
| Polysorbate 80 | 0.1 | in a conventional dairy homogenizer.

EXAMPLE 21

Ice Cream. Vanilla ice cream may be prepared by mixing

| Ingredient | parts |
|---|---|
| Sugar (10X) | 15.0 |
| Nonfat Dry Milk | 3.9 |
| Salt | 0.4 |
| into Water | 39.0 | for 3 minutes. Then add melted

| | |
|---|---|
| Example 6 Diol Diester | 28.4 | and cook to 200° F. while mixing. Hold for 1 minute. Cool to 169° F., and add

| | |
|---|---|
| Sugared Egg Yolks | 12.5 |
| Vanilla Extract | 0.8 | and mix 1 minute. Fill, then cool and freeze.

EXAMPLE 22

Filled Milk. To prepare a "filled milk" composition, combine about

| Ingredient | parts |
|---|---|
| Example 20 Filled Cream | 100 |
| Skim Milk | 900 | and rehomogenize.

EXAMPLE 23

Cheese Products. To prepare cheese products, treat

| Ingredient |
|---|
| Example 22 Filled Milk | made with a 1:1 mixture of Examples 1 and 6 diesters like natural milk in the normal cheese making process (as is practiced, for example in the production of Cheddar or Swiss cheese). Preferably add

| | parts |
|---|---|
| Butter Oil | 10 | to the fat mimetic portion of the filled milk product before it is employed in this process to enhance the proper flavor development of the cheese products.

EXAMPLE 24

Butter Cream Icing. Butter cream icing may be prepared by blending:

| Ingredient | parts |
|---|---|
| Sugar | 227.0 |
| Example 10 Diol Diester | 70.8 |
| Water | 28.4 |
| Nonfat Dry Milk | 14.0 |
| Emulsifier | 1.4 |
| Salt | 1.0 |
| Vanilla | 1.0 |

All of the ingredients are creamed in a mixer at medium speed.

EXAMPLE 25

Crackers. A dough prepared by mixing together

| Ingredient | parts |
|---|---|
| Flour | 100 |
| Sugar | 5.0 |
| Malt | 1.5 |
| Example 11 Diol Diester | 7.5 |
| Salt | 1.0 |
| Sodium Bicarbonate | 0.9 |
| Nonfat Dry Milk | 2.5 |
| High Fructose Corn Syrup | 2.5 |
| Monocalcium Phosphate | 0.75 |
| Water | 28 | is sheeted, stamped, and baked to produce a cracker product.

EXAMPLE 26

Sprayed Crackers. The sheeted and stamped cracker dough of Example 25 may be sprayed with the diol diester of Example 1 after baking.

EXAMPLE 27

Mayonnaise. Mayonnaise can be prepared from the following formulation:

| Ingredient | parts |
| --- | --- |
| Example 7 Diol Diester | 80 |
| Egg yolk | 5.5 |
| Vinegar | 3.0 |
| Salt | 1.5 |
| Sugar | 2.0 |
| Flavor | 0.5 |
| Water | 7.5 |

The egg yolk is first mixed with the other dry ingredients and a small amount of the water and vinegar in a container. The diester is then slowly poured into the container, while subjecting the container contents to mixing, to form an emulsion. While continuing to agitate the emulsion, the remaining water and vinegar is added.

EXAMPLE 28

Pudding. Pudding can be prepared from the following formulation:

| Ingredient | parts |
| --- | --- |
| Milk | 67 |
| Sugar | 11 |
| Starch | 5 |
| Water | 9 |
| Flavor | 3 |
| Example 8 Diol Diester | 5 |

The ingredients are blended together to form a pudding.

EXAMPLE 29

Frying Oil. The diol diester of Example 9 with 1 ppm polydimethylsiloxane may be used for frying food snacks. For frying potatoes, omit the polydimethylsiloxane.

EXAMPLE 30

Pet Food. Dry, expanded animal food kibs may be prepared from the following ingredients:

| Ingredient | parts |
| --- | --- |
| Hominy Feed | 37 |
| 52% Meat Meal | 17 |
| Wheat Shorts | 13 |
| Example 2 Diol Diester | 16 |
| Corn Germ Meal | 9.6 |
| Wheat Germ Meal | 3.0 |
| Dried Milk | 0.9 |
| Beet Pulp | 1.7 |
| Fish Scrap | 0.5 |
| Brewer's Yeast | 0.5 |
| Salt | 0.5 |
| Vitamins and Minerals | 0.1 |

The ingredients are mixed together and water added to raise the water content to 27%, before extrusion, pelleting, and drying in the usual manner.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition having a fat ingredient, wherein at least 5% of said fat ingredient comprises a fat mimetic compound of the formula

R—(CO)—O—(D)—O—(CO)—R', where D is an aliphatic group having 4 to 10 carbons, and R and R' are aliphatic groups having 1 to 29 carbons.

2. A composition according to claim 1 wherein said fat mimetic compound comprises at least 25% of said fat ingredient.

3. A composition according to claim 2 wherein said fat mimetic compound comprises 50 to 100% of said fat ingredient.

4. A composition according to claim 1 wherein the R and R' groups have 3 to 22 carbons.

5. A composition according to claim 1 wherein R and R' are derived from fatty acids selected from the group consisting of acetic, propionic, butyric, caproic, caprylic, pelargonic, capric, undecanoic, lauric, myristic, palmitic, stearic, arachidic, behenic, lignoceric, cerotic, montanic, palmitoleic, oleic, elaidic, vaccenic, linoleic, linolenic, eleostearic, arachidonic, erucic, brassidic, nervonic, eicosapentaenoic, docosatetraenoic, docosapentaenoic, and docosahexaenoic acid, and mixtures thereof.

6. A composition according to claim 1 wherein R and R' are derived from non-hydrogenated, partially hydrogenated or hydrogenated oils, fats or waxes selected from the group consisting of sunflower, high oleic sunflower, safflower, soybean, olive, sesame, peanut, palm kernel, cottonseed, mustard seed, palm, babassu nut, canola, rice bran, corn, rapeseed, high erucic rapeseed, low erucic rapeseed, borage, shea, meadowfoam, and marine oils, dairy butter, tallow, lard, and jojoba, and fractions thereof.

7. A composition according to claim 1 wherein said fat mimetic compound provides 0.5 to 8.5 kcal/gram upon being metabolized.

8. A method for reducing the available calories in a food composition having fat component, which method consists of at least partially replacing the fat component with a diol having 4 to 10 carbon atoms esterified with two $C_2$ to $CO_{30}$ fatty acids.

9. A method according to claim 8 wherein at least 5% of the fat component is replaced by said esterified diol.

10. A method according to claim 8 wherein said diol is selected from the group consisting of butanediol, butenediol, butynediol, pentanediol, pentenediol, pentynediol, hexanediol, hexenediol, hexynediol, heptanediol, heptenediol, heptynediol, octanediol, octenediol, octynediol, nonanediol, nonenediol, nonynediol, decanediol, decenediol, and decynediol.

11. A method according to claim 10 wherein said diol is selected from the group consisting of butanediol, pentanediol, hexanediol, heptanediol, nonanediol, and decanediol.

12. A method according to claim 8 wherein the fatty acids comprise acids having 4 to 23 carbons.

13. A method according to claim 8 wherein the fatty acids are selected from the group consisting of acetic, propionic, butyric, caproic, caprylic, pelargonic, capric, undecanoic, lauric, myristic, palmitic, stearic, arachidic, behenic, lignoceric, cerotic, montanic, palmitoleic, oleic, elaidic, vaccenic, linoleic, linolenic, eleostearic, arachidonic, erucic, brassidic, nervonic, eicosapentaenoic, docosatetraenoic, docosapentaenoic, and docosahexaenoic acid, and mixtures thereof.

14. A method according to claim 8 wherein the fatty acids are derived from non-hydrogenated, partially hydrogenated or hydrogenated oils, fats or waxes selected from the group consisting of sunflower, high oleic sunflower, safflower, soybean, olive, sesame, peanut, palm kernel, cottonseed, mustard seed, palm, babassu nut, canola, rice bran, corn, rapeseed, high erucic rapeseed, low erucic rapeseed, borage, shea, meadowfoam, marine oils, dairy butter, tallow, lard, and jojoba, and fractions thereof.

15. A method according to claim 8 wherein said esterified diols are partially digestible.

16. In a fat-containing food composition, an improvement wherein at least 5% of said fat ingredient is replaced by a $C_4$ to $C_{10}$ diol esterified with $C_2$ to $C_{30}$ fatty acids.

17. An improvement according to claim 16 wherein said esterified diol has the formula $$R-(CO)-O-(D)-O-(CO)-R',$$

where D is an alkyl group having 4 to 10 carbons, and R and R' are aliphatic groups having 3 to 22 carbons.

18. An improvement according to claim 17 wherein at least 80% of the R and R' groups have 17 carbons.

19. An improvement according to claim 16 wherein at least 25% of said fat ingredient is replaced by said esterified diol.

20. An improvement according to claim 19 wherein 50 to 100% of said fat ingredient is replaced by said esterified diol.

21. An improvement according to claim 20 wherein said esterified diol is partially digestible.

22. An improvement according to claim 16 wherein said food composition is a bakery product.

* * * * *